United States Patent [19]

Wade et al.

[11] 4,301,129
[45] Nov. 17, 1981

[54] SYNTHESIS OF NABH$_3$CN AND RELATED COMPOUNDS

[75] Inventors: Robert C. Wade, Ipswich; Benjamin C. Hui, Peabody, both of Mass.

[73] Assignee: Thiokol Corporation, Newtown, Pa.

[21] Appl. No.: 206,242

[22] Filed: Nov. 12, 1980

Related U.S. Application Data

[63] Continuation-in-part of Ser. No. 109,720, Jan. 4, 1980, abandoned, which is a continuation of Ser. No. 943,015, Sep. 18, 1978, abandoned.

[51] Int. Cl.$^3$ .......................... C01B 6/15; C07F 5/02
[52] U.S. Cl. .......................................... 423/284; 568/1
[58] Field of Search ............................ 423/284; 568/1

[56] References Cited

U.S. PATENT DOCUMENTS

| | | | |
|---|---|---|---|
| 3,634,277 | 1/1972 | Brown | 423/284 |
| 3,667,923 | 6/1972 | Wade et al. | 423/284 |
| 3,697,232 | 10/1972 | Wade et al. | 423/284 |

OTHER PUBLICATIONS

Wade et al.; "Inorg. Chem.", 9 1970, pp. 2146–2150.

*Primary Examiner*—G. O. Peters
*Attorney, Agent, or Firm*—G. K. White; R. J. Sheridan; R. E. Bright

[57] ABSTRACT

A process for the preparation of compounds of the formula RBH$_3$CN wherein R is an alkali metal, a quaternary ammonium radical or a phosphonium radical wherein a compound of the formula RCN is treated with a stoichiometric amount or slightly less than a stoichiometric amount of a BH$_3$ donor is described. The final products are useful as hydrolysis stable reductants and as synthetic intermediates.

6 Claims, 3 Drawing Figures

SYNTHESIS OF NABH₃CN AND RELATED COMPOUNDS

This is a continuation-in-part of Ser. No. 109,720 filed Jan. 4, 1980 which is a continuation of Ser. No. 943,015 filed Sept. 18, 1978, both now abandoned.

BACKGROUND OF THE INVENTION

This invention relates to the art of borohydrides, more specifically to cyanoborohydrides and processes for their preparation.

The preparation of lithium, sodium and quaternary ammonium cyanoborohydrides by reaction of anhydrous HCN with the appropriate borohydride salt is taught by U.S. Pat. No. 3,667,923. The preparation of potassium cyanoborohydride in analogous fashion is taught by U.S. Pat. No. 3,697,232. A detailed study of sodium cyanoborohydride preparation is given in Inorganic Chemistry, Vol. 9, page 2146 (1970). Copies of the patents and of the publication accompany this application for the examiner's convenience.

The present invention provides synthetic routes for the preparation of cyanoborohydrides in good yield, and in high purity with improved storage stability while avoiding the presence of HCN either as a reactant or a by-product of the reaction.

SUMMARY OF THE INVENTION

The invention provides a process for the preparation of a compound of the formula:

$$RBH_3CN$$

wherein R is an alkali metal, a quaternary ammonium radical, or a phosphonium radical, without the formation of substantial amounts of the isocyano isomer, i.e. $RBH_3NC$, which comprises treating a compound of the formula:

$$RCN$$

wherein R is as defined hereinabove with a $BH_3$ donor.

The tangible embodiments produced by this process aspect of the invention possess the inherent applied use characteristics of being known reducing agents for organic and inorganic compounds and of being, in aqueous solution, relatively more resistant to protonolysis than corresponding compounds $RBH_4$ wherein R is as defined hereinabove particularly at pH values below neutrality. The tangible embodiments produced by this process also are more storage stable than the products produced by U.S. Pat. No. 3,667,923. The tangible embodiments also possess the inherent applied use characteristic of being intermediates in the synthesis of known compounds with therapeutic utility in warm blooded animals.

Special mention is made of particular embodiments of the process of the invention wherein the $BH_3$ donor is $BH_3$.tetrahydrofuran. Special mention is also made of the process wherein $BH_3$.tetrahydrofuran is produced by a process which comprises treating a compound of the formula $RBH_4$ wherein R is as defined hereinabove with the molecular complex $BF_3$.tetrahydrofuran, of embodiments of the process of the invention wherein in the complete reaction sequence from the boron trifluoride.tetrahydrofuran molecular complex, treatment of the $BF_3$.tetrahydrofuran through the treatment of the cyanide compound is performed without separation of the $BH_3$.tetrahydrofuran complex from the by-products of its preparation and of the embodiments of the process of the invention wherein the $BH_3$.tetrahydrofuran complex is separated from the by-products of its preparation prior to treatment of the cyanide compound as a second step.

DESCRIPTION OF THE PREFERRED EMBODIMENT

Figure 1:
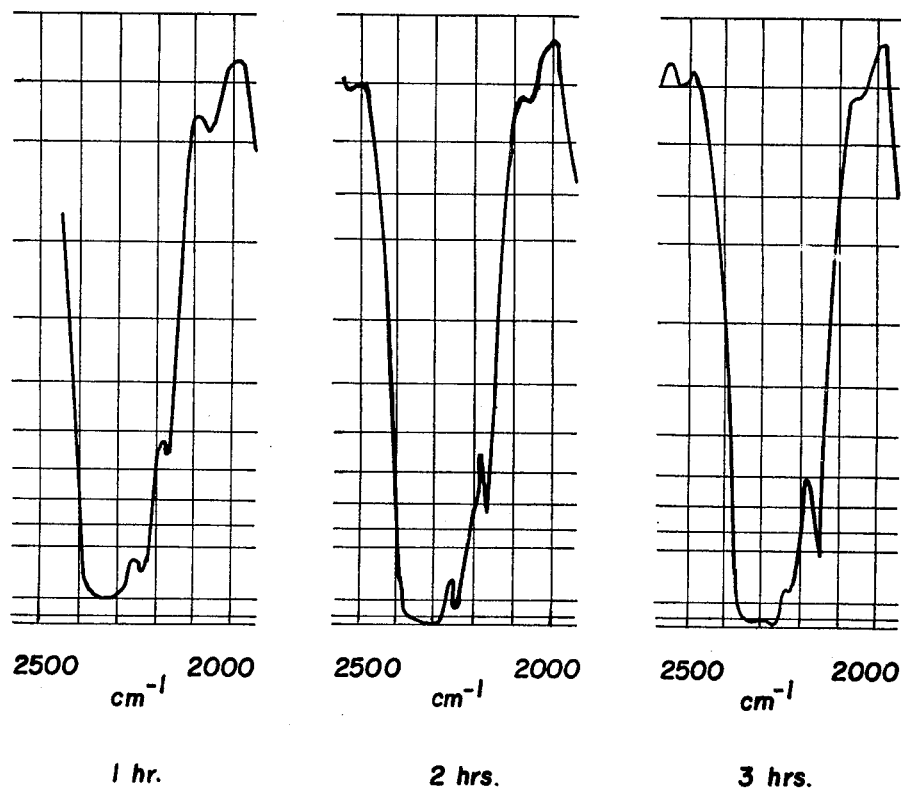
FIGS. 1-3 are segments of infrared spectra of a reaction mixture solution prepared according to this invention, taken at hourly intervals during the reflux step.

The manner of practicing the processes of the invention will now be described with reference to the preparation of a specific embodiment of the products thereof, namely, sodium cyanoborohydride ($NaBH_3CN$). To prepare sodium cyanoborohydride, sodium cyanide may be suspended in tetrahydrofuran and a solution of $BH_3$ in tetrahydrofuran may be added, while stirring, at as rapid a rate as can conveniently be accommodated by the apparatus. On a laboratory scale, a rate of addition of 1 liter of $BH_3$ solution per hour is convenient. The temperature of the mixture during the addition is not particularly critical and may range from $-10°$ C. to about 60° C., normal room temperature or slightly above, 20° C. to about 30° C., is preferred. The stoichiometry of the reaction is of course 1 mole of $BH_3$ to 1 mole of sodium cyanide, and it is preferred that the reaction be conducted with about a 5% excess of cyanide. After addition of the $BH_3$ solution is complete, the reaction may be stirred at about room temperature for up to about 5 additional hours. One skilled in the art will recognize that to insure the presence of only cyanoborohydride and the absence of iso adducts or higher homologues, a period of heating at temperatures of over 60° C. will be desirable. Heating at reflux for from one-half hour to 10 hours or longer, preferably about 7 hours, is convenient. Recovery of the product from the cooled reaction mixture after reflux may be by conventional techniques. Removal of undissolved material by filtration followed by evaporation of the filtrate is a convenient method. The reagents entering into the reaction should, naturally, be substantially anhydrous. Sodium cyanide is, of course, an article of commerce. Borane ($BH_3$) in tetrahydrofuran is commercially available. It may be prepared from boron trifluoride in diethylether by first replacing the diethyl ether with tetrahydrofuran by conventional techniques, adding the $BF_3$.diethyl ether to tetrahydrofuran and evaporating the diethyl ether is convenient, and then treating the $BF_3$.tetrahydrofuran solution with sodium borohydride.

The $BH_3$.tetrahydrofuran molecular complex so produced may either be purified by filtration and stabilized by the addition of a small quantity of sodium borohydride, or the treatment with sodium cyanide may be performed directly without separation of the by-products of generation of the $BH_3$.

The use of the tangible embodiments prepared by the invention are well-known in the literature.

Selectivity with sodium cyanoborohydride in the reduction of oximes, aldehydes and ketones and use in the selective introduction of deuterium is described by Borch et al in the Journal of the American Chemical Society, Vol. 93, page 2897 (1971). Similar use of lithium cyanoborohydride is reported by Borch in the Journal of the American Chemical Society, Vol. 91, page 3396 (1969). U.S. Pat. No. 3,647,890 is concerned with the use of lithium, sodium, potassium or quaternary ammonium cyanoborohydrides as reducing agents for ketones. Hutchins et al describe the reduction of alkyl iodides, bromides and tosylates with sodium cyanoborohydride in hexamethylphosphoramide in Chemical Communications (1971) page 1907. Kreevoy and Johnston describe the reduction of triphenylcarbinol to triphenylmethane in Croatica Chemica Acta, Vol. 45, page 511 (1973). The formation of nitrogen base donor cyanoborane addition compounds is described by Uppal and Kelly in Chemical Communications (1970) page 1619. The selective deoxygenation of aldehydes and ketones including hindered systems is described by Hutchins et al in the Journal of the American Chemical Society, Vol. 95, page 3662 (1973). The reduction of mono- and di-keto saturated steroids is described by Boutique et al in C. R. Acad. Sc. Paris, t.276, Serie C, page 437 (1973) and the reduction of conjugated steroidal ketones is described by Boutique et al in Bulletin de la Société Chemique de France (1973) page 3062. The selective reduction of aliphatic ketones and aldehydes to hydrocarbons with sodium cyanoborohydride and p-toluenesulfonyl hydrazide in dimethylformamide-sulfolane is described in Journal of the American Chemical Society, Vol. 93, page 1973 (1971). The selective reduction of primary iodides and, to a lesser extent, bromides to primary hydrocarbons with tetrabutylammonium cyanoborohydride in hexamethylphosphoramide is described in the Journal of the American Chemical Society, Vol. 95, page 6131 (1973). The reductive deoxygenation of $\alpha,\beta$-unsaturated p-tosylhydrazones with sodium cyanoborohydride is discussed by Hutchins et al in the Journal of Organic Chemistry, Vol. 40, page 923 (1975) and by Taylor and Djerassi in the Journal of the American Chemical Society, Vol. 98, page 2275 (1976). Selective reductions of $\alpha, \beta$-unsaturated esters, nitriles and nitro compounds with sodium cyanoborohydride are described by Hutchins et al in the Journal of Organic Chemistry, Vol. 41, page 3328 (1976). Hutchins and Kandasamy describe the reduction of conjugated aldehydes and ketones in acidic methanol and hexamethylphosphortriamide in the Journal of Organic Chemistry, Vol. 40, page 2530 (1975). The selective reduction of sugar iodides and tosylates with sodium cyanoborohydride is described by Kuzuhara et al in Carbohydrate Research (1975) Vol. 43 (2), page 293. Spielvogel and Bratton describe the preparation of macrocyclic cyanoboranes from sodium cyanoborohydride in the Journal of the American Chemical Society, Vol. 94, page 8597 (1972). Cure of sulfide containing polymers with lithium cyanoborohydride is described in U.S. Pat. No. 3,265,671. U.S. Pat. No. 3,637,516 describes bleaching liquor for ground wood pulp containing alkali metal cyanoborohydride as the reducing agent. Cyanotrihydroborate complexes of transition metals are described by Lippard and Welcker in Chemical Communications (1970) page 515 and Inorganic Chemistry, Vol. 11, page 6 (1972). Cationic ruthenium ammine complexes of cyanotrihydroborate are described by Ford in Chemical Communications (1971) page 7. Cyanotrihydroborato complexes of rhodium and iridium are described by Vaska et al in Chemical Communications (1971) page 1615. Photosensitive copper complexes suitable for image formation incorporating cyanotrihydroborate ion are described in U.S. Pat. No. 3,989,732. Chemical plating baths containing alkali metal cyanoborohydride are described in U.S. Pat. No. 3,637,472. An electroless gold plating bath containing alkali metal cyanoborohydride is described in U.S. Pat. No. 3,697,296. Use of cyanoborohydride anion to chemically fog a silver halide photographic emulsion is described in U.S. Pat. No. 3,951,656. The use of cyanoborohydride anion in the direct coupling of oligosaccharides to proteins and derivatized gels is described by Gray in Archives of Biochemistry and Biophysics, Vol. 163, page 426 (1974). Use of cyanoborohydride salts to reduce imminium compounds to amines is described in U.S. Pat. No. 3,873,621. Mild reduction of N,N'-mercuriobis-tosylhydrazones with sodium cyanoborohydride, synthesis of N-arylmethyl-N'-tosylhydrazines and deoxygenation of aromatic ketones is described by Rosini et al in Synthesis (1976) page 530. Selective reductions with sodium cyanoborohydride in the course of determination of the sterochemistry of octopine and its isomers and their enzymic properties are described by Biellmann et al in Bioorganic Chemistry (1977) Vol. 6 (1) 89. The use of sodium cyanoborohydride in the synthesis of biradical nitroxides is described by Rauckman et al in Org. Prep. Proced. Int. (1977) Vol. 9 (2) page 53. Amine catalysis of the reduction of ketones by sodium cyanoborohydride is described by Chow in Tung Wu Shu Li Hsueh Pao (1975) page 139. A general synthesis of amine cyanoboranes from sodium cyanoborohydride and the antitumor activity and hypolipidemic activity of $Me_3N-BH_2COOH$ and its N-ethylamide derivative both prepared from $Me_3N-BH_2CN$ are described in Inorganic Chemistry, Vol. 17, page 2327 (1978). The use of sodium cyanoborohydride in the N-methylation of amides and related compounds by reduction of methylols is described by Basha et al in Synthetic Communications, Vol. 7, page 549 (1977).

$BH_3$.tetrahydrofuran molecular complex or $BH_3$diethyl ether molecular complex may also be prepared by passing gaseous diborane into the desired solvent and stabilizing the resulting solution with a small quantity of sodium borohydride.

One skilled in the art will recognize that in place of the sodium cyanide illustrated, one may substitute other cyanide salts of alkali metals such as lithium, potassium, rubidium or cesium or of quaternary ammonium ions, which are either commercially available, obtainable by neutralization of HCN, preferably in aqueous solution, with a stoichiometric amount of the appropriate base followed by freeze drying of the solution of the salt, or by conventional ions exchange techniques, to prepare the other cyanoborohydrides contemplated as obtainable through the processes of the invention. The term quaternary ammonium radical contemplates a tetra substituted nitrogen atom of the general formula

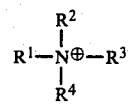

wherein $R^1$, $R^2$, $R^3$, and $R^4$ are independently lower alkyl of 1 to about 20 carbon atoms, alkenyl of about 3 to about 20 carbon atoms, cycloalkyl of 3 to about 6 carbon atoms, mono carbocyclic aryl of about 6 carbon atoms, mono carbocyclic aryl alkyl of from 7 to about 11 carbon atoms, halo, amino, carboxy, alkoxy carbonyl, nitrile, or hydroxyl alkyl of from 1 to about 6 carbon atoms, alkoxy alkyl of 2 to 22 carbon atoms, or mono carbocyclic aryl hydroxy alkyl of from 7 to about 15 carbon atoms, or when taken together with the nitrogen atom to which they are attached, any two of $R^1$, $R^2$, $R^3$ or $R^4$ may be concatenated to form a 5 or 6 membered heterocyclic ring containing carbon, hydrogen, oxygen or nitrogen, said heterocyclic rings and said monocarbocyclic aryl groups being unsubstituted or halo, hydroxy, amino, or mono or dialkyl substituted, said alkyl groups being straight, branched chain or cyclic and containing 1 to 6 carbon atoms.

Illustrative of these are quaternary ammonium ions such as tetramethyl, tetraethyl, tetrapropyl, tetra-isopropyl, tetra-n-butyl, tetra-i-butyl, t-butyl trimethyl, phenyl trimethyl, benzyl trimethyl, cyclohexyl-triethyl, allyl trimethyl, 2-chloroethyl-trimethyl, 2-hydroxybutyl trimethyl, tri-(2-hydroxy ethyl) methyl, 2-ethoxypropyl trimethyl, α-amino-p-tolyl trimethyl, 3-cyanopropyl trimethyl, 2-carboxy-ethyl trimethyl, amyl dimethyl phenyl, cetyl trimethyl, tricapryl methyl, piperidinium dimethyl, morpholinium diethyl, pyrrolidinium dimethyl, piperazinium cyclohexyl methyl, 1-methyl-piperidinum dimethyl, 4-ethylmorpholinium dipropyl, 1-isopropyl-pyrrolidinium dimethyl, 1,4-dimethyl-piperazinium-diethyl, 1-n-butylpiperidinium-di-methyl, 2-methyl-piperidinium diethyl, 1-ethyl-2-methyl-piperidinium dipropyl-, tetraethanol, diethyl-diethanol, tri-n-butyl mono-ethanol, tris(hydroxymethyl) methyl, phenyl-d-methyl mono-ethanol, and the like.

One skilled in the art will also recognize that, although the processes of the invention have been illustrated through use of tetrahydrofuran as a preferred solvent, any inert solvent in which the reactants and products have reasonable solubility, as well as mixtures thereof, may be employed as equivalents. Typical examples of these solvents are ethers containing from about 4 to about 10 carbon atoms, such as, diethyl ether, the dimethyl ethers of ethylene glycol, diethylene glycol, triethylene glycol and the like, as well as dimethyl formamide and dimethyl sulfide. It will similarly be obvious that mixtures of two or more of these solvents may be employed.

One skilled in the art will recognize that, although the process of the invention has been illustrated by use of a $BH_3$.tetrahydrofuran molecular complex as a $BH_3$ donor, any compound or molecular complex capable of donating $BH_3$ may be employed as an equivalent. Typical examples of these are: diborane, $BH_3$.dimethylsulfide, or $BH_3$ in a molecular complex with the aforementioned ethers containing from about 4 to about 10 carbon atoms.

One skilled in the art will also recognize that $BF_3$-diethyl ether complex may be utilized to prepare $BH_3$.tetrahydrofuran complex without intermediate conversion to a $BF_3$.tetrahydrofuran complex.

In addition to the quaternary ammonium moieties illustrated hereinabove as suitable for use in the practice of the invention, one skilled in the art will recognize that analogous phosphonium cyanides may be treated in analogous fashion with $BH_3$ donors to prepare the phosphonium cyanoborohydride embodiments contemplated as being produced by the processes of this invention.

The following examples further illustrate the best mode contemplated by the inventors for the practice of their invention.

EXAMPLE 1

Conversion of $BF_3$-Diethyl Ether Comples to $BF_3$.Tetrahydrofuran Complex Add boron trifluoride-diethyl-etherate (275 ml, 2.18 moles) to tetrahydrofuran (190 ml, 2.35 moles) in a vessel equipped for suction and stirring. The mixture is stirred at room temperature under reduced pressure until substantially all diethyl ether is removed. Removal of the diethyl ether may, if desired, be followed by gas chromatography.

EXAMPLE 2

Borane-Tetrahydrofuran Complex from Boron Trifluoride-Tetrahydrofuran Complex Sodium borohydride (62.74 g., 1.658 moles) is suspended in tetrahydrofuran (810 ml) under a nitrogen atmosphere and cooled to about 5° C. The boron trifluoride-tetrahydrofuran complex of Example 1 is added slowly with stirring over a period of about 2 hours. Stirring is continued for about ½ hour after the addition is complete. Filtration through a pressure filter under nitrogen into a vessel cooled in an ice bath gives the title product (1.7 molar) in tetrahydrofuran solution (800 ml.). Sodium borohydride (0.7 g., 0.0185 mole) is added to stabilize the solution.

EXAMPLE 3

Sodium Cyanoborohydride

Sodium cyanide (114.9 g., 2.344 moles) is suspended in tetrahydrofuran (200 ml) under a nitrogen atmosphere at about ambient temperature (22° C.). The cooled (ice-bath) borane-tetrahydrofuran solution from Example 2 is then added slowly while stirring under nitrogen. Addition requires about one hour and the reaction is stirred for an additional 5 hours at room temperature, then heated at reflux for about 10 hours. After cooling, the reaction mixture is filtered and the filtrate evaporated to dryness in vacuo at 60° C. to give the title product as a white powder which is further dried in a vacuum oven (1 hour at room temperature, 24 hours at 90° C.), 82.0 g.

Analysis for $NaBH_3CN$: Calc: H,4.81%; B,17.20%; CN,41.40% Found: H,4.45%; B,15.69%; CN,37.43%.

Repetition of the processes of Examples 2 and 3 results in product yields ranging from 59 to 71%, based on the boron trifluoride-tetrahydrofuran complex, which yields are low due to the relatively low conversion of boron trifluoride-tetrahydrofuran complex to borane-tetrahydrofuran complex.

EXAMPLE 4

Preparation of Sodium Cyanoborohydride Directly From Boron Trifluoride-Tetrahydrofuran Complex Without Isolation of The Intermediate Borane-Tetrahydrofuran Complex Sodium borohydride (65.70 g., 1.737 moles) is suspended in tetrahydrofuran (810 ml) and cooled in an ice bath while under a nitrogen atmosphere. Boron trifluoride-tetrahydrofuran complex (2.18 moles) prepared as in Example 1 is added by a procedure analogous to that of Example 2. After a post addition stirring period of 1.5 hours, sodium cyanide (112.7 g., 2.299 moles) is added slowly in small batches while continuing cooling. When addition is complete, the reaction mixture is stirred for 5 hours at room temperature and then heated at reflux for 10 hours. After cooling and filtration under $N_2$, the filtrate is evaporated and the residue dried as in Example 3 to obtain the title product 116.6 g.

Analysis for $NaBH_3CN$ Calc: H,4.81%; B,17.20%; CN,41.40%. Found: H,4.60%; B,16.89%; CN,33.14%.

Repetition of this procedure results in yields of from 85 to 88% of theoretical, based on boron-trifluoride-tetrahydrofuran complex.

EXAMPLE 5

Preparation of Boron-Tetrahydrofuran Complex Directly From Boron Trifluoride-Diethyl Ether Complex Following a procedure generally analogous to that of Example 2, from $NaBH_4$ (79.67 g., 2.11 m.), $BF_3$.diethyl ether complex (2.69 m., 340 ml.) and tetrahydrofuran (1000 ml.) is obtained a 1.5 molar solution of borane-tetrahydrofuran complex (900 ml.).

EXAMPLE 6

Preparation of Sodium Cyanoborohydride from the Borane-Tetrahydrofuran Complex of Example 5

Following a procedure analogous to that of Example 3, there is obtained from the product solution of Example 5 and sodium cyanide (80 g), 85.1 g. of sodium cyanoborohydride.

Analysis for $NaBH_3CN$ Calc: H,4.81%; B,17.20%; CN,41.40%. Found: H,4.14%; B,16.05%; CN,35.38%.

EXAMPLES 7–10

These examples illustrate the preparation of borane-tetrahydrofuran complex ($BH_3 \cdot THF$) from $NaBH_4$ and boron trifluoride-diethyl ether complex ($BF_3$.ether) or boron trifluoride-tetrahydrofuran complex ($BF_3 \cdot THF$). The reaction proceeds according to the equation:

$$3\ NaBH_4 + 4\ BF_3 \cdot X \xrightarrow{THF} 4\ BH_3 \cdot THF + 3\ NaBF_4$$

where X=ether or THF. Quantities of reactants used and product yields are indicated in Table I below. This general procedure is as follows:

$NaBH_4$ and tetrahydrofuran (THF) are placed in a 3-neck flask having a pressure equalized dropping funnel, reflux condenser and mechanical stirrer connected thereto. The flask and $NaBH_4$/THF mixture contained therein is cooled in an ice bath and purged with $N_2$ for 1 hour. $BF_3 \cdot X$ is transferred to the dropping funnel under a blanket of $N_2$ and added slowly dropwise to the $NaBH_4$/THF mixture at a rate of about 120 ml/hr. The $N_2$ flow is stopped during the $BF_3 \cdot X$ addition. After the addition of $BF_3 \cdot X$ is complete, the mixture is stirred for at least 1 hour before the $BH_3 \cdot THF$ produced is pressure filtered into a flask which is cooled in an ice bath.

EXAMPLES 11–14

These examples illustrate the preparation of sodium cyanoborohydride ($NaBH_3CN$) by reacting, each in turn, the products of Examples 7–10 and NaCN.

The general procedure for the preparation of $NaBH_3CN$ is as follows:

A 5 mole % excess of NaCN is suspended in THF in a 2 liter flask. The flask is then purged with $N_2$ for 1 hour. $BH_3 \cdot X$ is added to the flask rapidly dropwise at a rate of about 1 liter/hr. while maintaining a slow stream of $N_2$ through the flask. After the addition of $BH_3 \cdot X$ is complete, the mixture is stirred for about 5 hours. The resulting reaction mixture is heated under reflux for about 10 hours under a stream of $N_2$. The resulting mixture is cooled and pressure filtered. The filtrate is dried under a rotary evaporator at 55° C. The resulting product is $NaBH_3CN$ and is obtained in a typical purity of about 90% and in the yields indicated in Table II.

Figure 2:
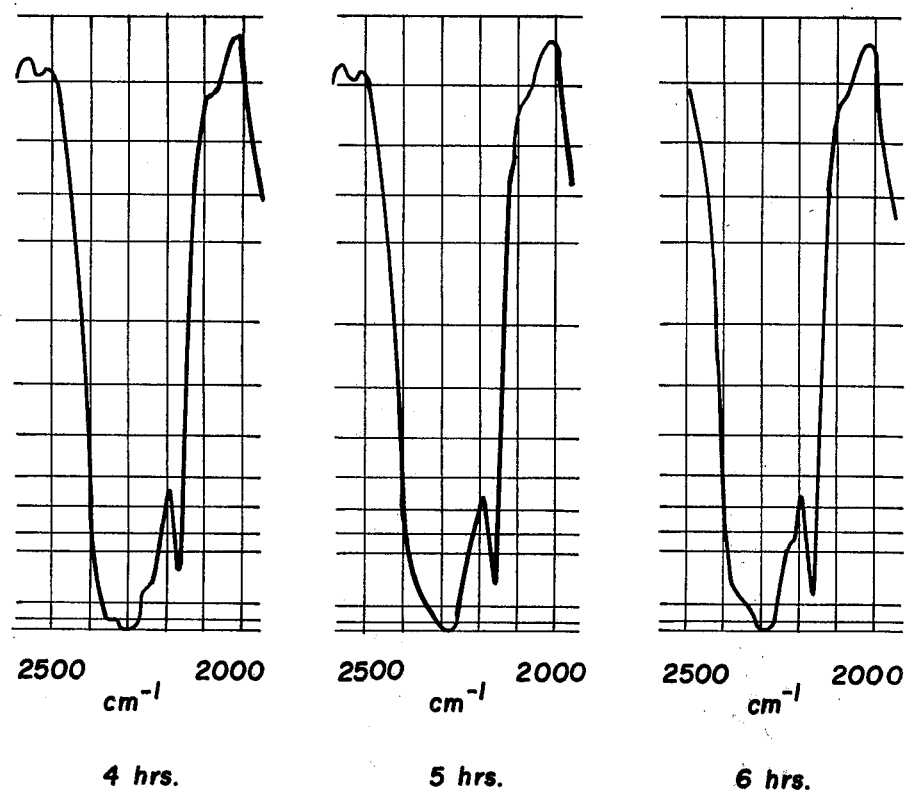
Figure 3:
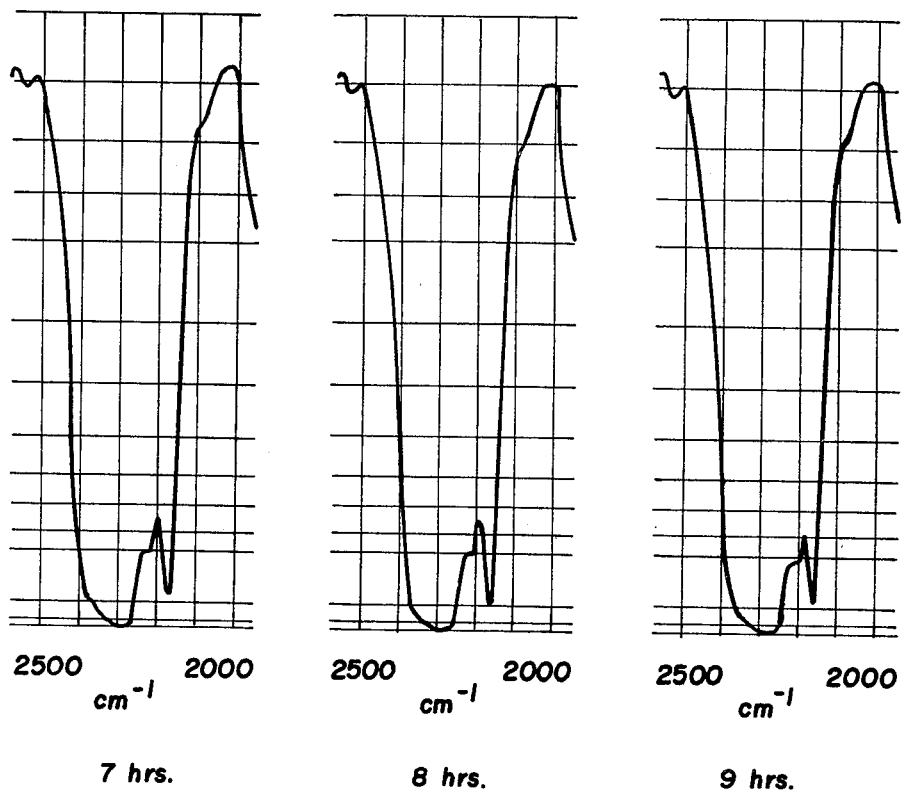

The purpose of heating the reaction mixture under reflux is to convert $NaBH_3CN$ and $NaBH_3CNBH_3$ produced during the reaction to the desired product, $NaBH_3CN$. FIGS. 1–3 illustrate this conversion.

The graphs in FIGS. 1–3 are segments of the infrared spectra of a typical reaction mixture solution of Examples 11–14 taken at hourly intervals during the reflux step. The bands of the spectra are associated with the various compounds present in the reaction mixture as follows:

| Band | Compound |
|---|---|
| 2075 cm$^{-1}$ | $NaBH_3NC$ |
| 2260 cm$^{-1}$ | $NaBH_3CNBH_3$ |
| 2240 cm$^{-1}$ | $NaBH_3CN$ |

FIGS. 1–3 clearly illustrate that, at the beginning of the reflux period, the primary compounds present in the reaction mixture are $NaBH_3NC$ and $NaBH_3CNBH_3$. However, as the reaction mixture is heated under reflux, the bands associated with $NaBH_3CNBH_3$ (2260 cm$^{-1}$) and $NaBH_3NC$ (2075 cm$^{-1}$) begin to disappear and a new band (2240 cm$^{-1}$), associated with $NaBH_3CN$, forms. After approximately 7 hours of heating under reflux, the bands associated with $NaBH_3NC$ and $NaBH_3CNBH_3$ have virtually disappeared and the band associated with $NaBH_3CN$ has reached essentially maximum intensity.

Thus, the spectra in FIGS. 1–3 clearly indicate the conversion of the undesirable products $NaBH_3NC$ and $NaBH_3CNBH_3$ to the desired product $NaBH_3CN$ during the reflux step.

TABLE I

| Example No. | $NaBH_4$ moles | $BF_3$ . ether moles | $BF_3$ . THF moles | Mole Ratio $BF_3/NaBH_4$ | Total Volume Solvent, ml$^{(a)}$ | [$BH_3$ . THF], M Calc. M$^{(b)}$ | Found | % Conversion of $BH_3$ . THF |
|---|---|---|---|---|---|---|---|---|
| 7 | 3.29 | 3.96 | — | 1.204 | 1412 | 2.83 | 2.10 | $^{(c)}$ |
| 8 | 3.04 | — | 3.96 | 1.303 | 1825 | 2.17 | 1.60 | 73.7 |
| 9 | 1.74 | — | 2.18 | 1.253 | 1000 | 2.18 | 1.86 | 85.3 |
| 10 | 1.66 | — | 2.18 | 1.315 | 1000 | 2.18 | — | — |

$^{(a)}$Volume of THF + volume of ether or THF in $BF_3$ . X
$^{(b)}$Concentration is calculated assuming no solvent is lost
$^{(c)}$Can not be estimated due to loss of diethyl ether during the reaction

TABLE II

| Example No. | NaBH$_3$CN moles | % Yield NaBH$_3$CN Based on BF$_3$ | % Yield NaBH$_3$CN Based on BH$_3$ |
| --- | --- | --- | --- |
| 11 | 1.66 | 41.9 | — |
| 12 | 2.63 | 66.4 | 96.7 |
| 13 | 1.85 | 84.9 | 99.5 |
| 14 | 1.29 | 59.2 | — |

EXAMPLE 15

This example illustrates the stability of sodium cyanoborohydride, prepared according to the process of this invention.

Samples of the sodium cyanoborohydride prepared in Examples 11–14 and a sample of sodium cyanoborohydride prepared in accordance with the general teachings of U.S. Pat. No. 3,697,232 (i.e. using HCN as starting material instead of NaCN) are each stored in closed bottles at room temperature (18°–25° C.). This latter sample turns black and loses 50% of its active hydride content after 2 to 3 months storage at room temperature. Samples 1 to 5 retain their initial white color and are free flowing.

The initial hydride analysis and that after the storage period indicated for each sample is:

| Product of Example No. | Initial H$^-$% | Storage H$^-$% (time) |
| --- | --- | --- |
| 11 | 4.46 | 4.36 (4 months) |
| 12 | 3.98 | 4.20 (3 months) |
| 12$^{(d)}$ | 4.47 | 4.47 (3 months) |
| 13 | 4.60 | 4.46 (3 months) |
| 14 | 4.45 | 4.38 (3 months) |

$^{(d)}$Recrystallized product of Example 12

This data indicates the improved storage stability of sodium cyanoborohydride prepared according to the process of this invention.

EXAMPLE 16

Borane Tetrahydrofuran Complex in Tetrahydrofuran from Diborane

Pass diborane gas (2270 g., 82 moles) into tetrahydrofuran (164 l.) under argon at a rate of 30–35 cu.ft. per min. After addition is complete, analyze for borane concentration by standard techniques (hydrolysis and titration of boric acid so formed is a convenient method). Add sodium borohydride (0.19 g., 0.005 moles per mole of retained BH$_3$) to stabilize the solution.

EXAMPLE 17

Potassium Cyanoborohydride from Potassium Cyanide and Diborane

Treat suspension of potassium cyanide (1 mole) in dimethylformamide with diborane (0.5 mole) under conditions analogous to those described in Example 3 to prepare the title product in dimethylformamide solution.

The subject matter which applicants regard as their invention is particularly pointed out and distinctly claimed as follows:

1. A process for the preparation of cyanoborohydrides having the formula:

RBH$_3$CN wherein R is an alkali metal, a quaternary ammonium radical, or a phosphonium radical, said process comprising:

(a) reacting a cyanide compound of the formula:

RCN wherein R is a defined above, and a BH$_3$ donor, and
(b) heating the reaction product of (a) under refluxing conditions until substantially all of any isocyanoborohydride produced in step (a) is converted to cyanoborohydride.

2. A process as defined in claim 1 wherein the BH$_3$ donor is the molecular complex BH$_3$.tetrahydrofuran.

3. A process as defined in claim 2 wherein the molecular complex BH$_3$.tetrahydrofuran is prepared by treating the molecular complex BF$_3$.diethyl ether with a compound of the formula RBH$_4$ wherein R is an alkali metal, a quaternary ammonium radical or a phosphonium radical.

4. A process as defined in claim 3 wherein the molecular complex BH$_3$.tetrahydrofuran is separated from the by-products of its preparation prior to treatment of the cyanide compound with said complex.

5. A process as defined in claim 3 wherein the treatment of the cyanide compound with the BH$_3$.tetrahydrofuran molecular complex is commenced without separation of said complex from the by-products of its preparation.

6. A process as defined in claims 1, 2, 3, 4 or 5 wherein R is sodium.

* * * * *